(12) United States Patent
Petit

(10) Patent No.: US 11,544,112 B1
(45) Date of Patent: *Jan. 3, 2023

(54) TASK PROCESSING UTILIZING QUEUES

(71) Applicant: ALLSCRIPTS SOFTWARE, LLC, Chicago, IL (US)

(72) Inventor: Jason Daniel Petit, Rochester, IL (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/728,839

(22) Filed: Dec. 27, 2019

Related U.S. Application Data

(63) Continuation of application No. 15/722,533, filed on Oct. 2, 2017, now Pat. No. 10,565,013, which is a continuation of application No. 14/942,596, filed on Nov. 16, 2015, now Pat. No. 9,778,955, which is a (Continued)

(51) Int. Cl.
| | |
|---|---|
| *H04L 12/26* | (2006.01) |
| *G06F 9/50* | (2006.01) |
| *H04L 43/50* | (2022.01) |
| *G06Q 10/06* | (2012.01) |
| *G06Q 50/22* | (2018.01) |
| *G06Q 50/00* | (2012.01) |
| *H04L 47/70* | (2022.01) |
| *H04L 43/103* | (2022.01) |
| *G16H 10/60* | (2018.01) |
| *G16H 50/20* | (2018.01) |

(Continued)

(52) U.S. Cl.
CPC ......... *G06F 9/50* (2013.01); *G06Q 10/06311* (2013.01); *G06Q 10/063114* (2013.01); *G06Q 50/00* (2013.01); *G06Q 50/22* (2013.01); *G16H 10/60* (2018.01); *G16H 40/20* (2018.01); *G16H 50/20* (2018.01); *H04L 43/103* (2013.01); *H04L 43/50* (2013.01); *H04L 47/70* (2013.01); *H04L 63/10* (2013.01)

(58) Field of Classification Search
CPC ....... H04L 43/103; H04L 43/00; H04L 67/12; H04L 47/70; H04L 63/10; G06Q 10/06316; G06Q 10/06311; G06Q 10/063114; G06Q 50/22; G06Q 50/00; G16H 10/60; G16H 50/20; G16H 40/20; G06F 9/50

See application file for complete search history.

(56) References Cited

U.S. PATENT DOCUMENTS 9,191,299 B1 11/2015 Petit
9,778,955 B2 10/2017 Petit
(Continued)

*Primary Examiner* — Jungwon Chang
(74) *Attorney, Agent, or Firm* — Loza & Loza, LLP; Peter Zura

(57) ABSTRACT

A system includes a plurality of queues configured to hold tasks and state information associated with such tasks. The system further includes a plurality of listeners configured to query one of the plurality of queues for a task, receive, in response to querying one of the plurality of queues for a task, a task together with state information associated with the task, effect processing of the received task, and communicate a result of the received task to another queue of the plurality of queues, the another queue of the plurality of queues being selected based on the processing of the received task.

20 Claims, 16 Drawing Sheets

Related U.S. Application Data continuation of application No. 14/320,309, filed on Jun. 30, 2014, now Pat. No. 9,191,299.

(60) Provisional application No. 61/943,424, filed on Feb. 23, 2014, provisional application No. 61/943,375, filed on Feb. 22, 2014.

(51) Int. Cl.
   *G16H 40/20*    (2018.01)
   *H04L 9/40*     (2022.01)

(56) References Cited

U.S. PATENT DOCUMENTS

| | | | | |
|---|---|---|---|---|
| 2007/0074211 A1* | 3/2007 | Klug | ............... | G06Q 10/06 718/100 |
| 2008/0120620 A1* | 5/2008 | Lett | ............... | G06F 9/485 718/103 |
| 2008/0164998 A1 | 7/2008 | Scherpbier et al. | | |
| 2010/0094656 A1* | 4/2010 | Conant | ............... | G16H 10/60 705/3 |
| 2010/0251248 A1 | 9/2010 | Hosouchi et al. | | |
| 2011/0321051 A1 | 12/2011 | Rastogi | | |
| 2012/0042039 A1 | 2/2012 | Mark | | |
| 2013/0145299 A1 | 6/2013 | Steimle et al. | | |
| 2013/0198759 A1 | 8/2013 | Shah et al. | | |
| 2013/0253969 A1 | 9/2013 | Das et al. | | |
| 2014/0095203 A1 | 4/2014 | Anand et al. | | |
| 2014/0108035 A1 | 4/2014 | Akbay et al. | | |
| 2014/0136255 A1* | 5/2014 | Grabovski | ............... | G06Q 10/063112 705/7.14 |
| 2014/0258759 A1 | 9/2014 | Mital et al. | | |
| 2014/0297297 A1* | 10/2014 | Head | ............... | G16H 50/20 705/2 |
| 2014/0330589 A1* | 11/2014 | Tran | ............... | G16H 10/60 705/3 |
| 2015/0234997 A1 | 8/2015 | Sarrafzadeh et al. | | |

\* cited by examiner

TASK PROCESSING UTILIZING QUEUES

CROSS-REFERENCE TO RELATED APPLICATION

This is a continuation of U.S. patent application Ser. No. 15/722,533 filed Oct. 2, 2017, which is a continuation of U.S. patent application Ser. No. 14/942,596 filed Nov. 16, 2015, now U.S. Pat. No. 9,778,955 issued Oct. 3, 2017, which is a continuation of U.S. patent application Ser. No. 14/320,309 filed Jun. 30, 2014, now U.S. Pat. No. 9,191,299 issued Nov. 17, 2015, which claims the benefit of priority to U.S. Provisional Application No. 61/943,375 filed Feb. 22, 2014 and U.S. Provisional Application No. 61/943,424 filed Feb. 23, 2014, each of which are incorporated herein by reference in their entirety.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to task processing.

Traditionally, single-threaded systems are limited by how fast each item can be processed. Further, in processing workflows, with some systems, an error later in the workflow can leave the system in an inconsistent state, or can cause loss of data.

Additionally, scaling traditional systems can be difficult. Physical servers must be shut down to add resources. Virtual machines can scale up (add resources), but traditional systems wouldn't allow scaling out (adding nodes).

A need exists for improvement in task processing. This need, as well as other needs, is addressed by one or more aspects of the present invention.

SUMMARY OF THE INVENTION

The present invention includes many aspects and features. Moreover, while many aspects and features relate to, and are described in, the context of health care, the present invention is not limited to use only in this context, as will become apparent from the following summaries and detailed descriptions of aspects, features, and one or more embodiments of the present invention.

Accordingly, one aspect of the present invention relates to a method comprising polling, by a first queue listener loaded on a first server, a first queue; receiving, at the first queue listener loaded on the first server in response to the polling by the first queue listener of the first queue, a first task and state information associated with the first task; executing, at the first server, the first task utilizing the state information associated with the first task; communicating, from the first server to a second queue, a first result of the first task, the first result including state information; polling, by a second queue listener loaded on a second server, the second queue; receiving, at the second queue listener loaded on the second server in response to the polling by the second queue listener of the second queue, a second task based on the first result communicated from the first server to the second queue, together with state information associated with the second task that is based on the state information included in the first result; executing, at the second server, the second task utilizing the state information associated with the second task; communicating, from the second server to a third queue, a second result of the second task, the result including state information; polling, by a third queue listener loaded on a third server, the third queue; receiving, at the third queue listener loaded on the third server in response to the polling by the third queue listener of the third queue, a third task based on the second result communicated from the second server to the third queue, together with state information associated with the third task that is based on the state information included in the second result; executing, at the third server, the third task utilizing the state information associated with the third task; and communicating, from the third server to a fourth queue, a third result of the third task.

In a feature of this aspect, the first server comprises an electronic device.

In a feature of this aspect, the first server comprises one or more electronic devices.

In a feature of this aspect, the second server comprises an electronic device.

In a feature of this aspect, the second server comprises one or more electronic devices.

In a feature of this aspect, the third server comprises an electronic device.

In a feature of this aspect, the third server comprises one or more electronic devices.

In a feature of this aspect, the method further comprises communicating a confirmation of completion of the first task.

In a feature of this aspect, the method further comprises displaying, at a display associated with an electronic device, information to a user based on the third result.

In a feature of this aspect, the method further comprises displaying, at a display associated with an electronic device, a notification to a user based on the third result.

In a feature of this aspect, the method further comprises displaying, at a display associated with an electronic device, a notification associated with a patient health care order to a user based on the third result.

In a feature of this aspect, the method further comprises displaying, at a display associated with an electronic device, a notification of a rule violation of a patient health care order to a user based on the third result.

In a feature of this aspect, the method further comprises displaying, at a display associated with an electronic device, a notification associated with a patient health care order to a user.

In a feature of this aspect, the method further comprises displaying, at a display associated with an electronic device, a notification of a rule violation of a patient health care order to a user.

In a feature of this aspect, executing, at the third server, the third task utilizing the state information associated with the third task comprises determining whether a rule of a health care order has been violated.

In a feature of this aspect, executing, at the third server, the third task utilizing the state information associated with the third task comprises effecting communication of a notification.

In a feature of this aspect, executing, at the third server, the third task utilizing the state information associated with the third task comprises effecting communication of a notification that a rule of a health care order has been violated.

In a feature of this aspect, executing, at the third server, the third task utilizing the state information associated with the third task comprises effecting communication of a notification that a patient is non-compliant with a health care order.

Another aspect relates to a method which includes polling, by a first queue listener loaded on a first server, a first queue; receiving, at the first queue listener loaded on the first server in response to the polling by the first queue listener of the first queue, a first task and state information associated with the first task; executing, at the first server, the first task utilizing the state information associated with the first task; communicating, from the first server to a second queue, a first result of the first task, the first result including state information; polling, by a second queue listener loaded on a second server, the second queue; receiving, at the second queue listener loaded on the second server in response to the polling by the second queue listener of the second queue, a second task based on the first result communicated from the first server to the second queue, together with state information associated with the second task that is based on the state information included in the first result; executing, at the second server, the second task utilizing the state information associated with the second task; and communicating, from the second server, a result of the second task.

Another aspect relates to a non-transitory computer readable medium containing computer executable instructions for performing a disclosed method.

Another aspect relates to a system which includes a plurality of queues configured to hold tasks and state information associated with such tasks. The system further includes a plurality of listeners configured to query one of the plurality of queues for a task, receive, in response to querying one of the plurality of queues for a task, a task together with state information associated with the task, effect processing of the received task, and communicate a result of the received task to another queue of the plurality of queues, the another queue of the plurality of queues being selected based on the processing of the received task.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
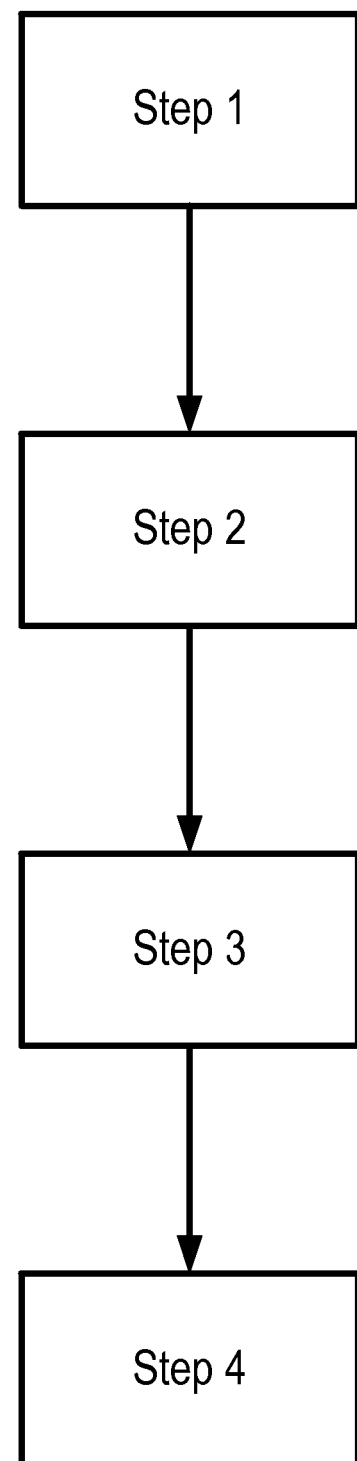
FIG. 1 illustrates an exemplary process which includes four steps.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

In one or more preferred implementations, a system utilizes queues, queue listeners, and tasks to implement a methodology. In one or more preferred implementations, such a methodology can be characterized as utilizing dependency inversion.

In an exemplary methodology, for each step of a workflow, there is a queue listener. This listener periodically polls an incoming queue for tasks. When a task is found, the item is generally marked as in progress, the task is executed, a resulting task is placed in an outgoing queue, and finally the task is removed from the incoming queue. The next step of the workflow treats the previous outgoing queue as its incoming queue, and the process continues. If an error occurs, the task will, after a timeout, be re-pulled to try again. If a task fails a certain number of times, the task is preferably added to a failure repository (e.g. to be examined by a support team). In one or more preferred implementations, because the tasks are stored in persistent queues and current state is stored with the task, new server instances can be created to process items on the fly. In one or more preferred implementations, if certain steps of the workflow require minimal resources, the queue listeners for different queues are started on the same server (potentially at the cost of losing the ability to scale steps individually).

For illustrative purposes, consider an exemplary process comprising four steps, as illustrated in FIG. 1. In an exemplary implementation, a queue will be set up for each of these steps, as illustrated in FIG. 2.

In one or more preferred implementations, one or more queue listeners periodically poll a step queue for a task that needs to be performed (e.g. an instance of that step). In one or more preferred implementations, queue listener may be configured to only poll a single step queue, while in one or more preferred implementations a queue listener may be configured to poll multiple step queues.

Figure 2:
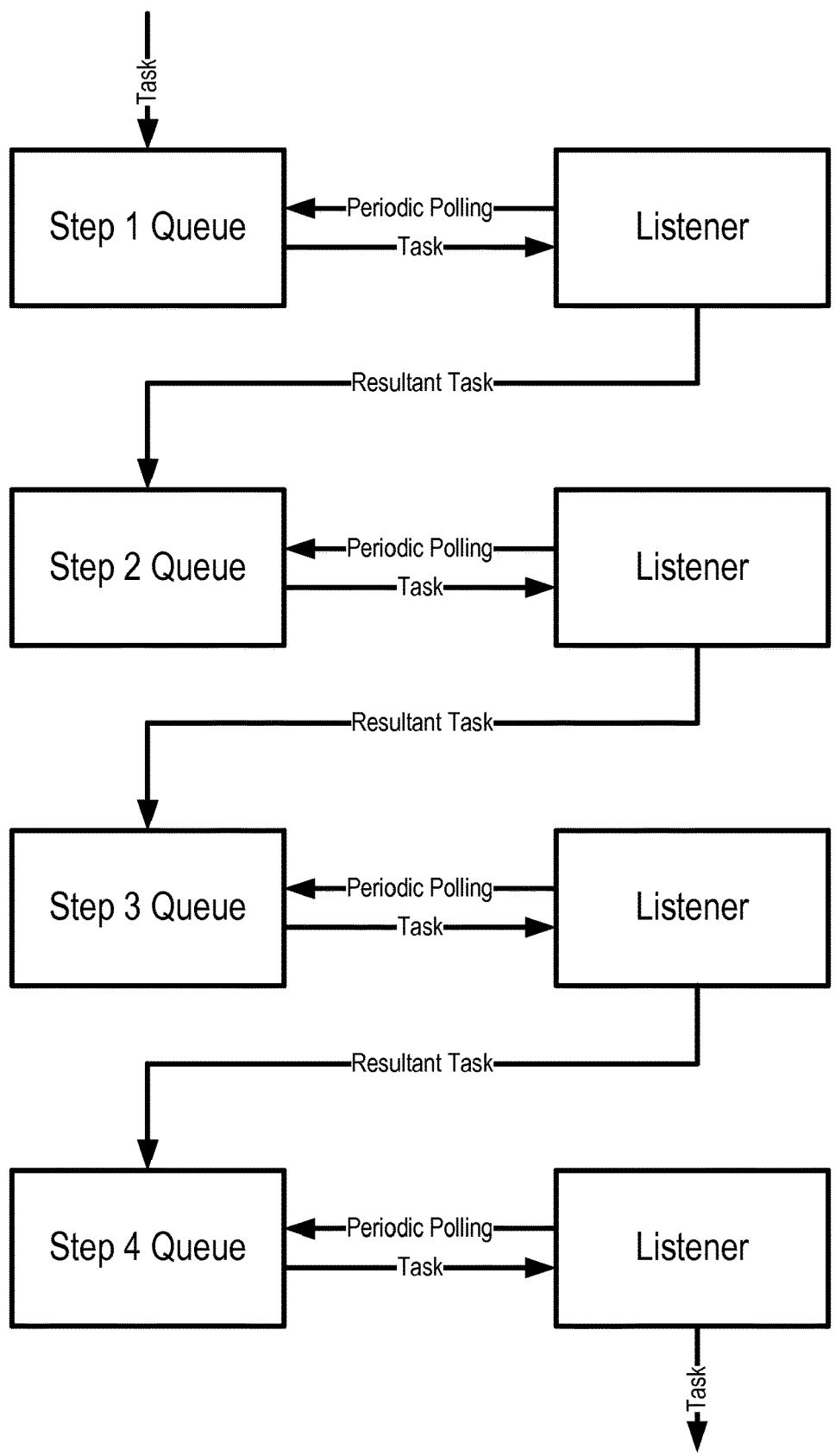
FIGS. 2-6 illustrate the use of listeners to handle tasks from queues.

When a task is found, the task is generally marked as in progress, the task is executed, and a resulting task is placed into a subsequent queue, as illustrated in FIG. 2. This process can be repeated for each step.

Figure 3:
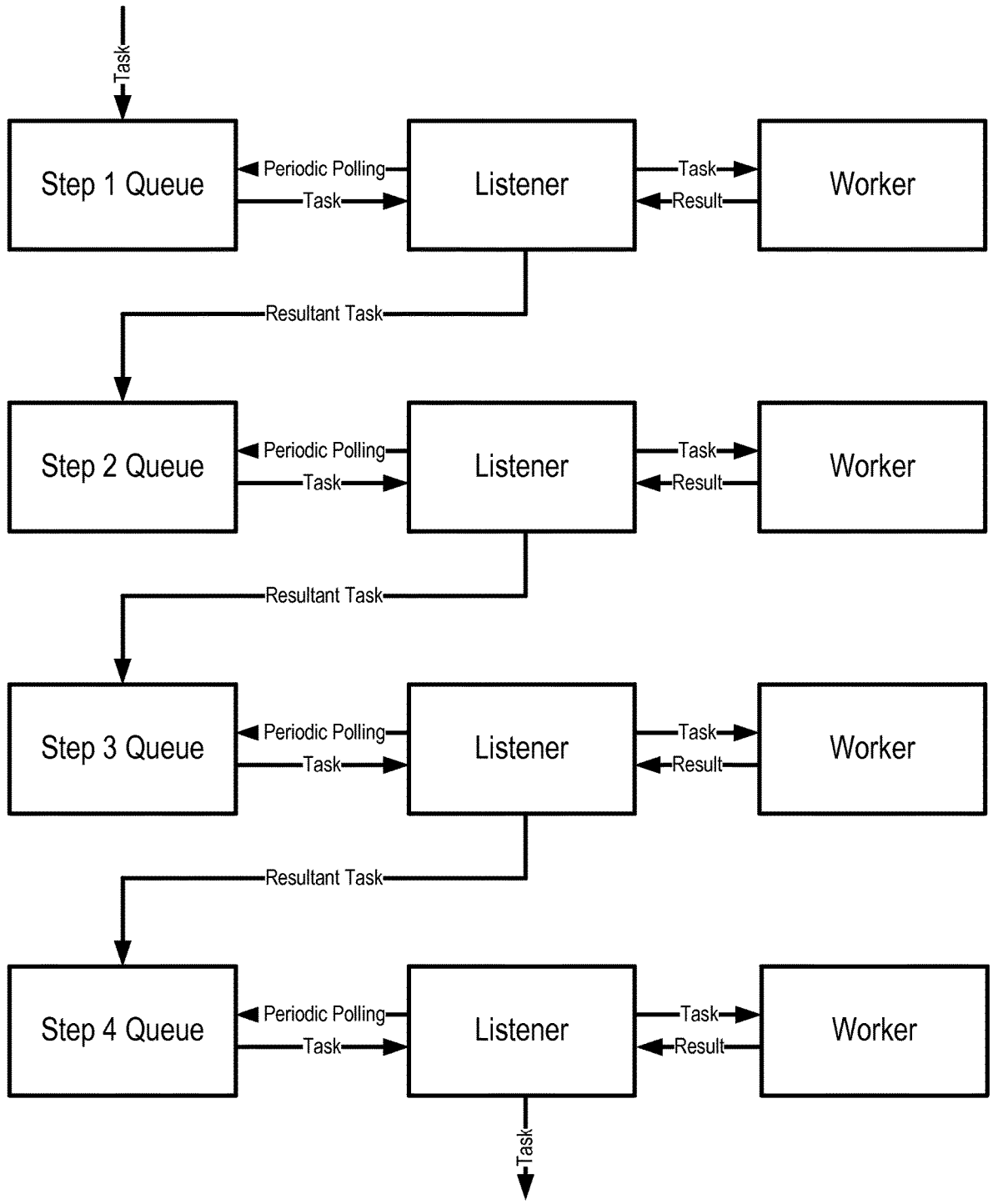
Figure 4:
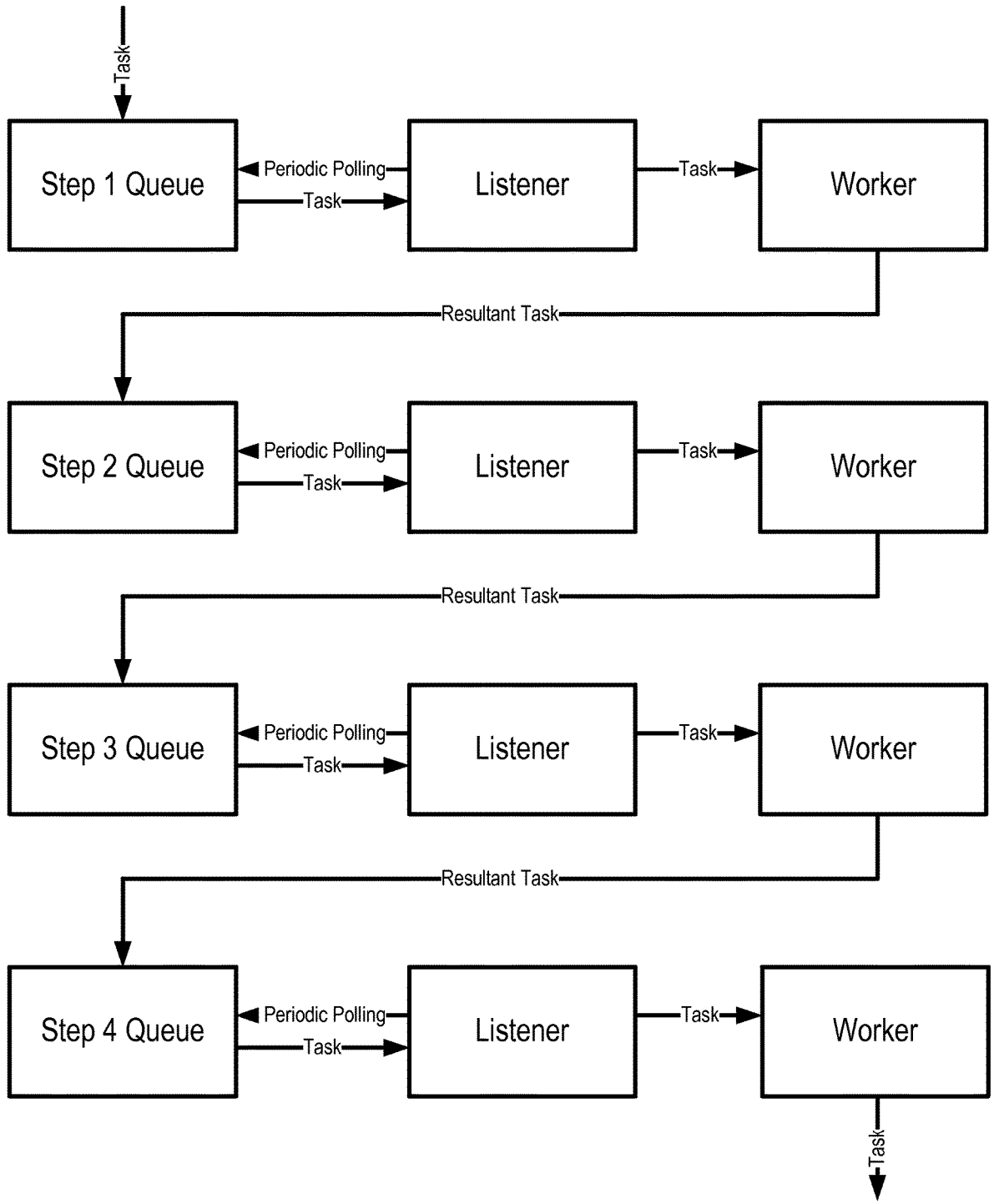

In one or more preferred implementations, rather than execute a task itself, listener may be configured to assign a task to a worker, as illustrated in FIG. 3. In one or more preferred implementations, a worker may return a result to the listener who may pass it on to another queue, as illustrated in FIG. 3, or the worker itself may pass a result to another queue, as illustrated in FIG. 4.

Figure 5:
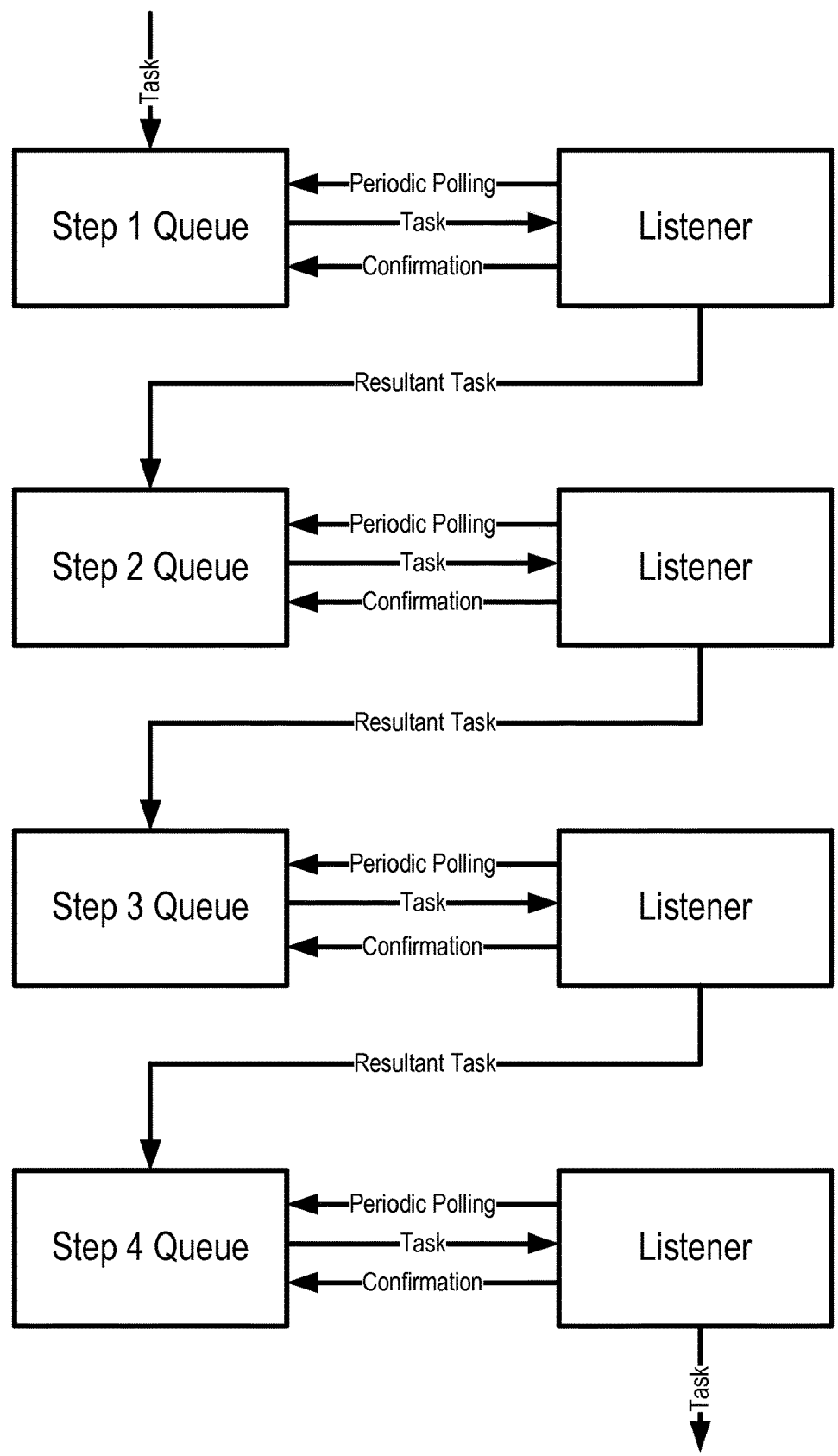

In one or more preferred implementations, upon completion of a task, confirmation that the task has been completed is returned to the queue the task came from, as illustrated in FIG. 5. For example, in one or more preferred implementations, a task is indicated to be in progress once it has been sent to a listener, and is then marked completed and removed from the queue once confirmation has been received that the task has been completed. In one or more preferred implementations, if confirmation of completion is not received for a task that has been sent to a listener without a defined time frame, then the task is considered to have failed to be completed and is placed back in the queue for sending out to another listener.

Figure 6:
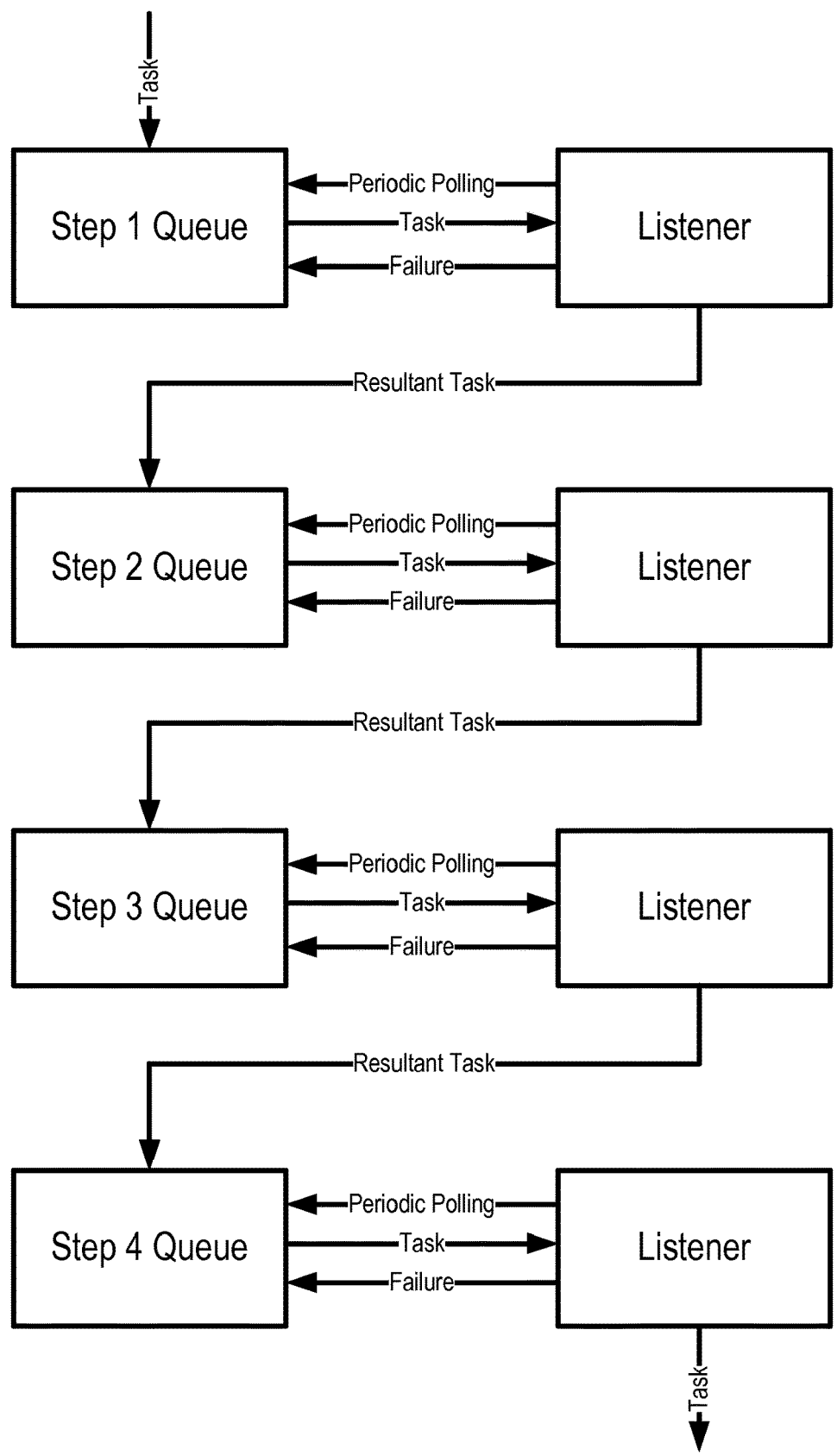
Figure 7:
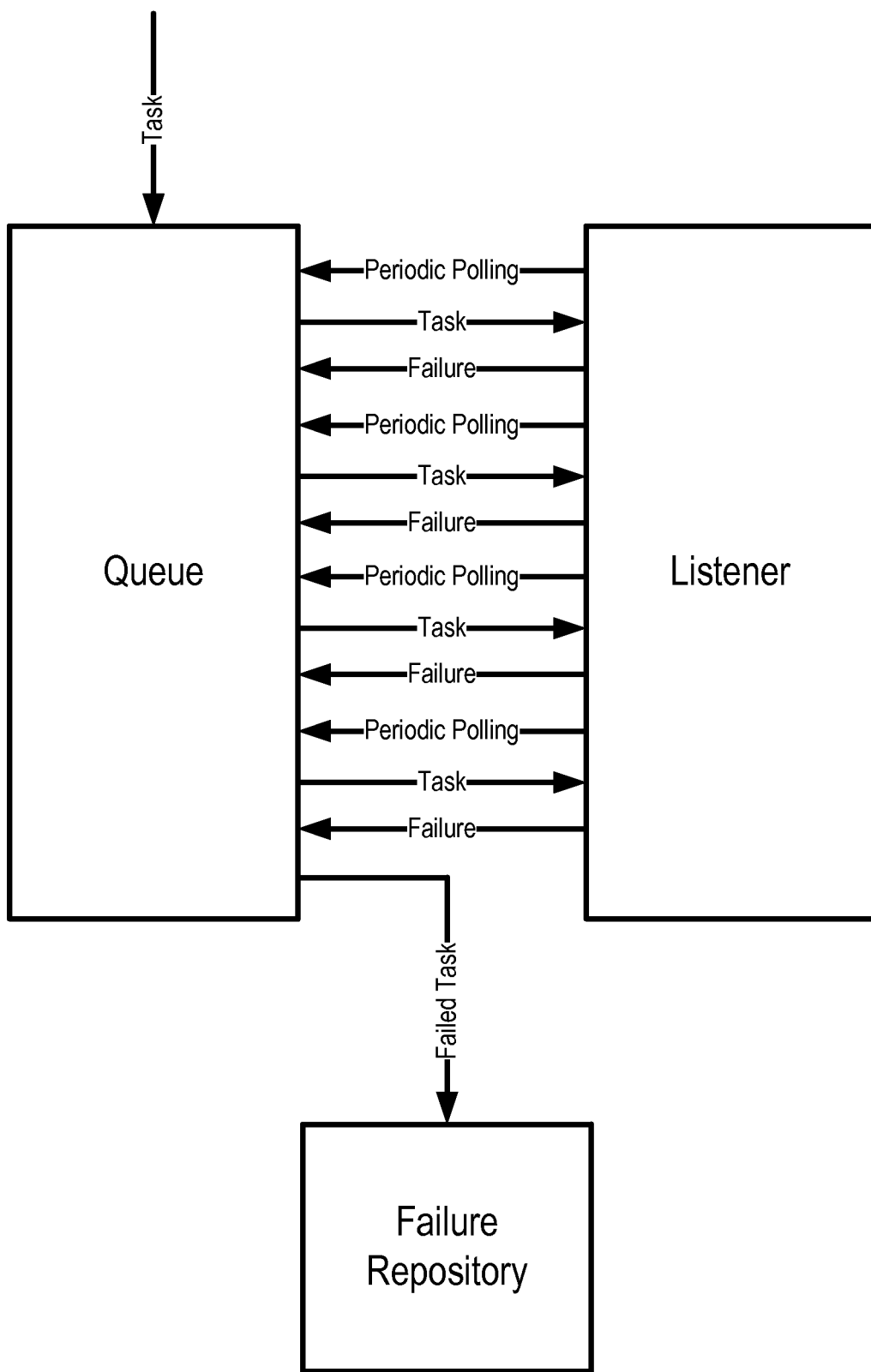
FIG. 7 illustrates the use of a failure repository.

Additionally or alternatively, in one or more preferred implementations, a listener that fails to complete a task may communicate a failure message back to a queue, as illustrated in FIG. 6. The failure message may include an indication of the task that failed to be completed or a copy of the task itself. In one or more preferred implementations, repeated failures of a task may cause the task to be placed into a failure repository, as illustrated in FIG. 7.

Figure 8:
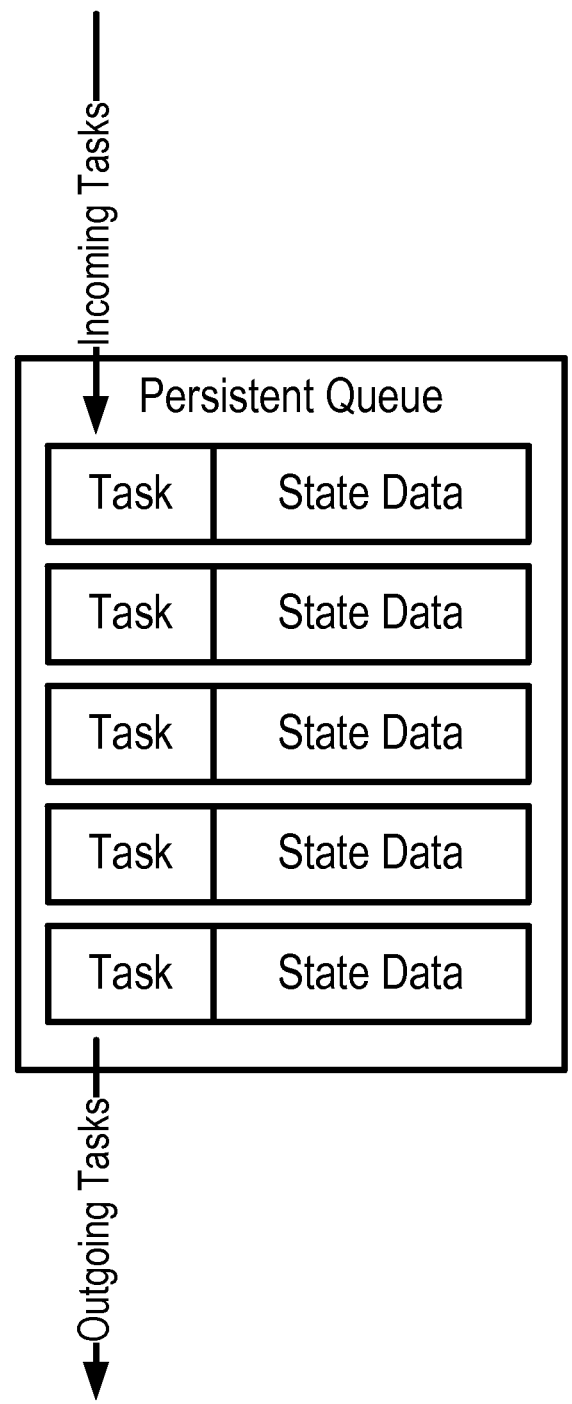
FIG. 8 illustrates the storage of state data with tasks in a persistent queue.
Figure 9:
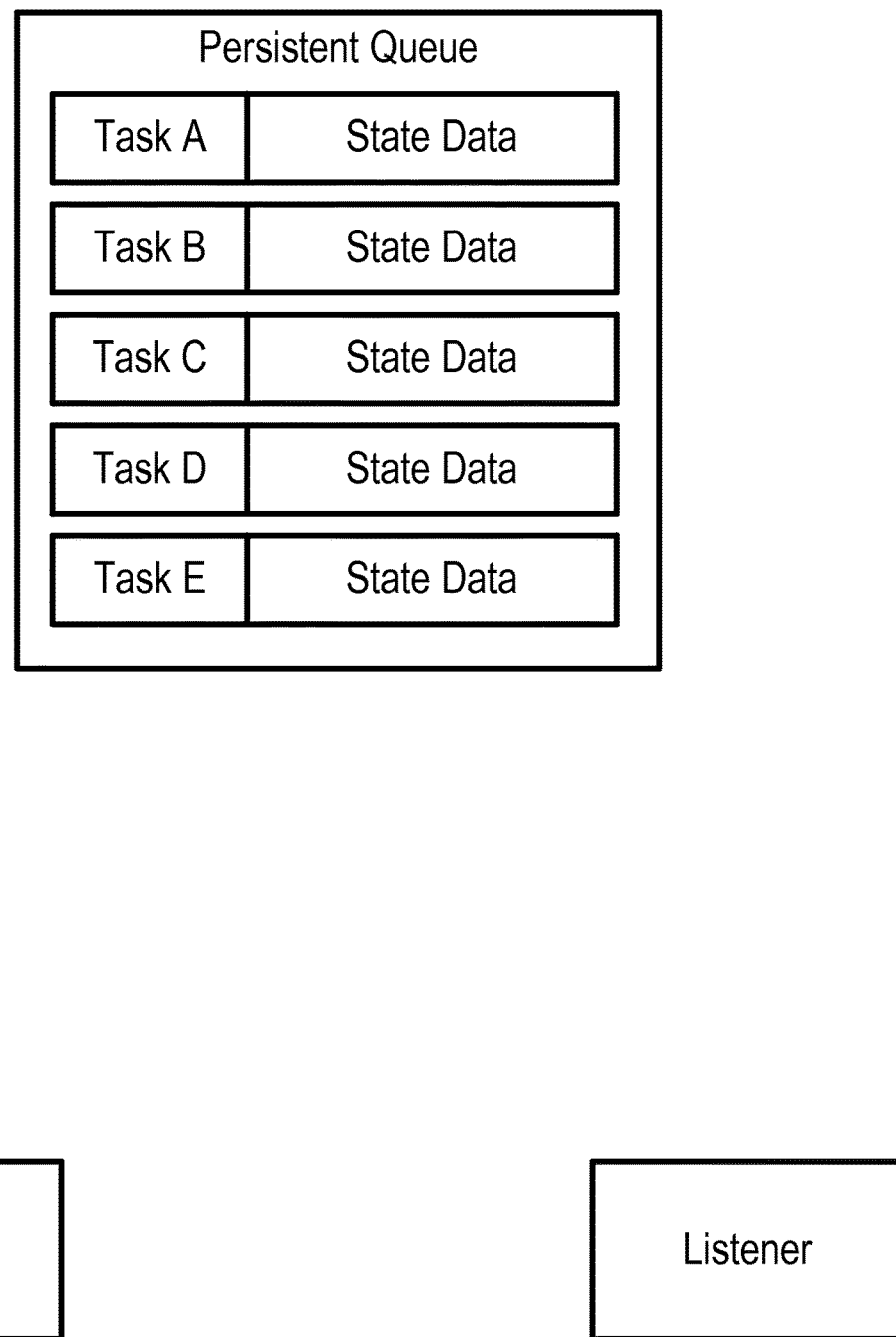
FIGS. 9-13 illustrate use of several listeners to process tasks of a persistent queue.
Figure 10:
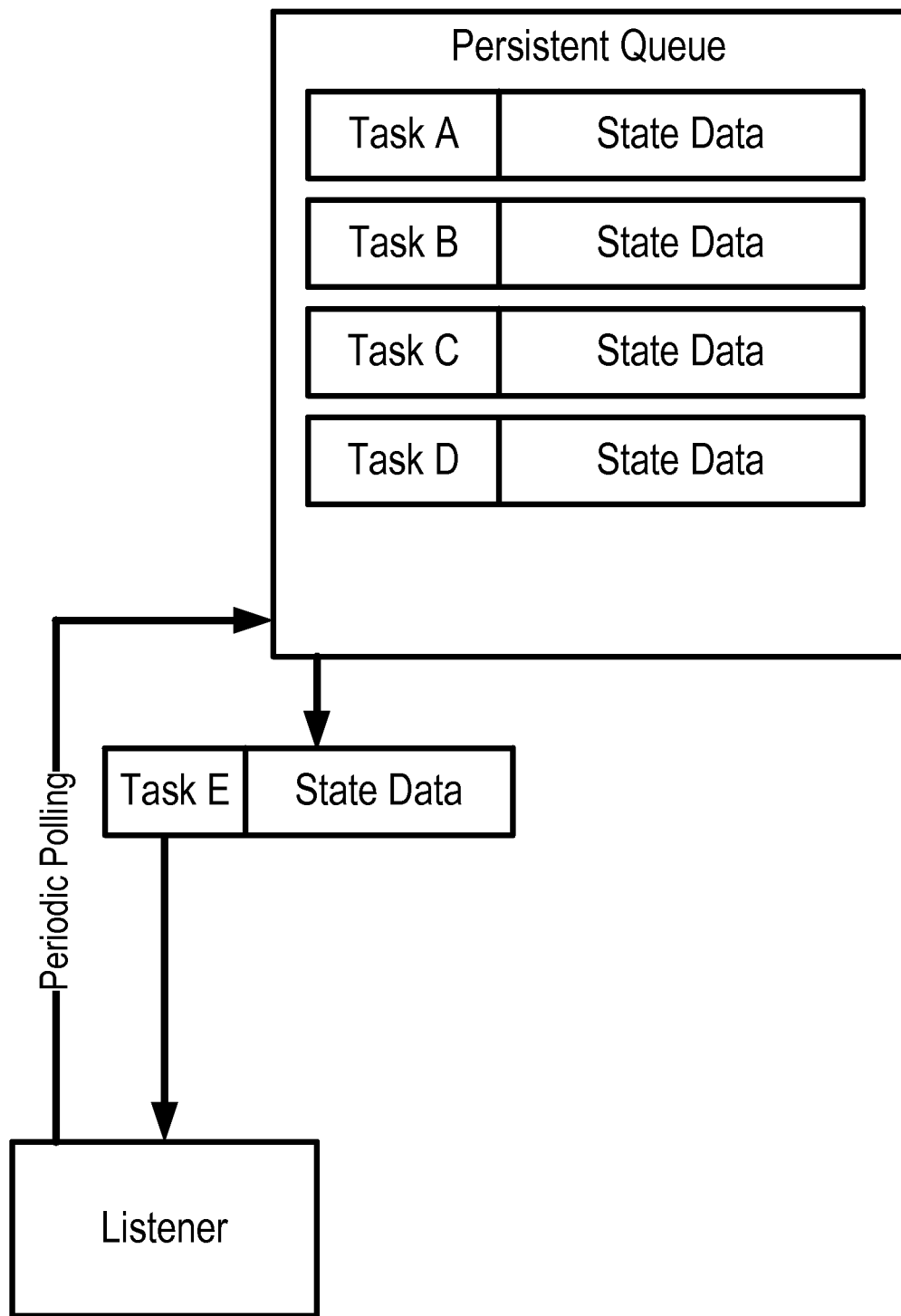
Figure 11:
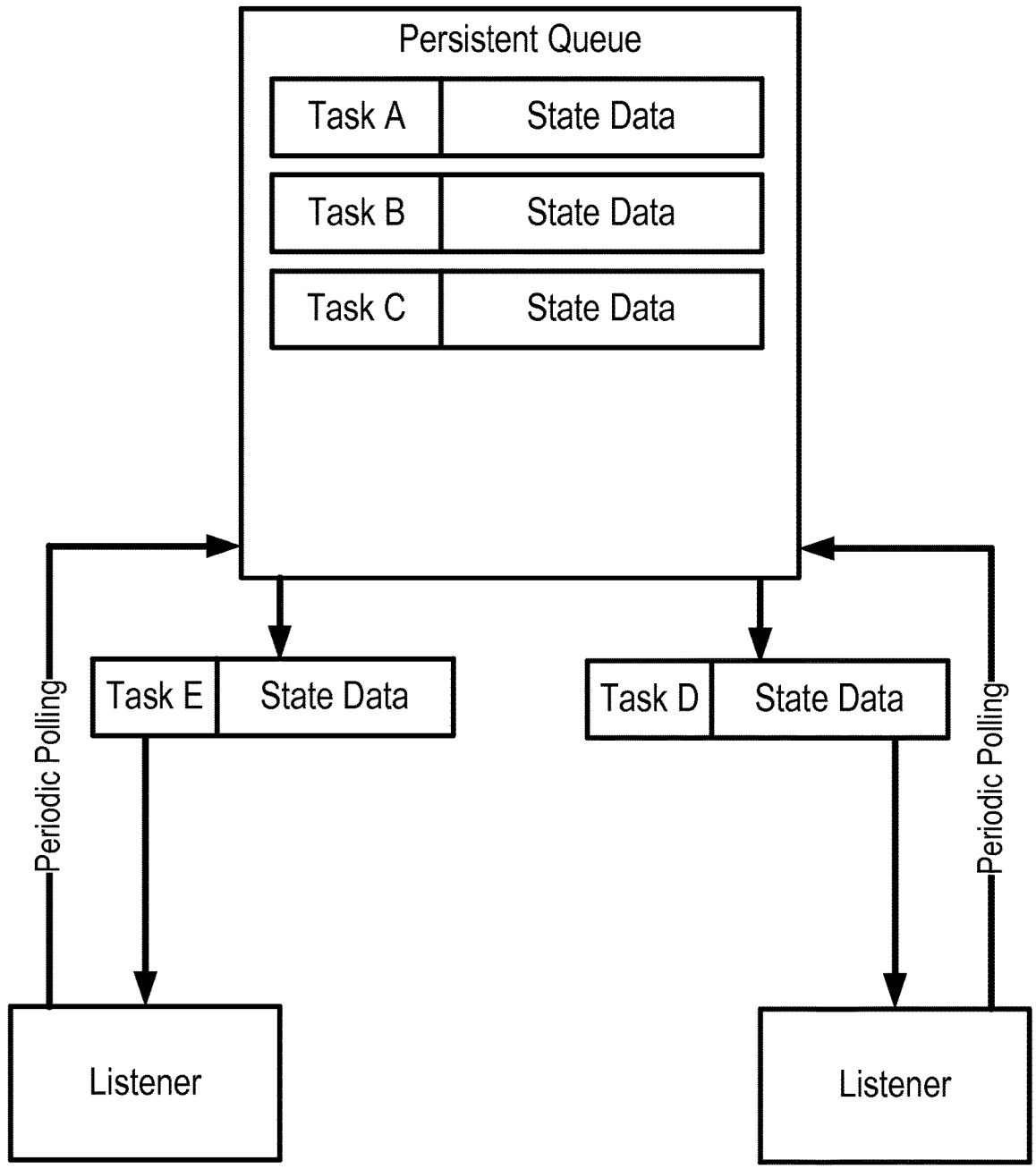
Figure 12:
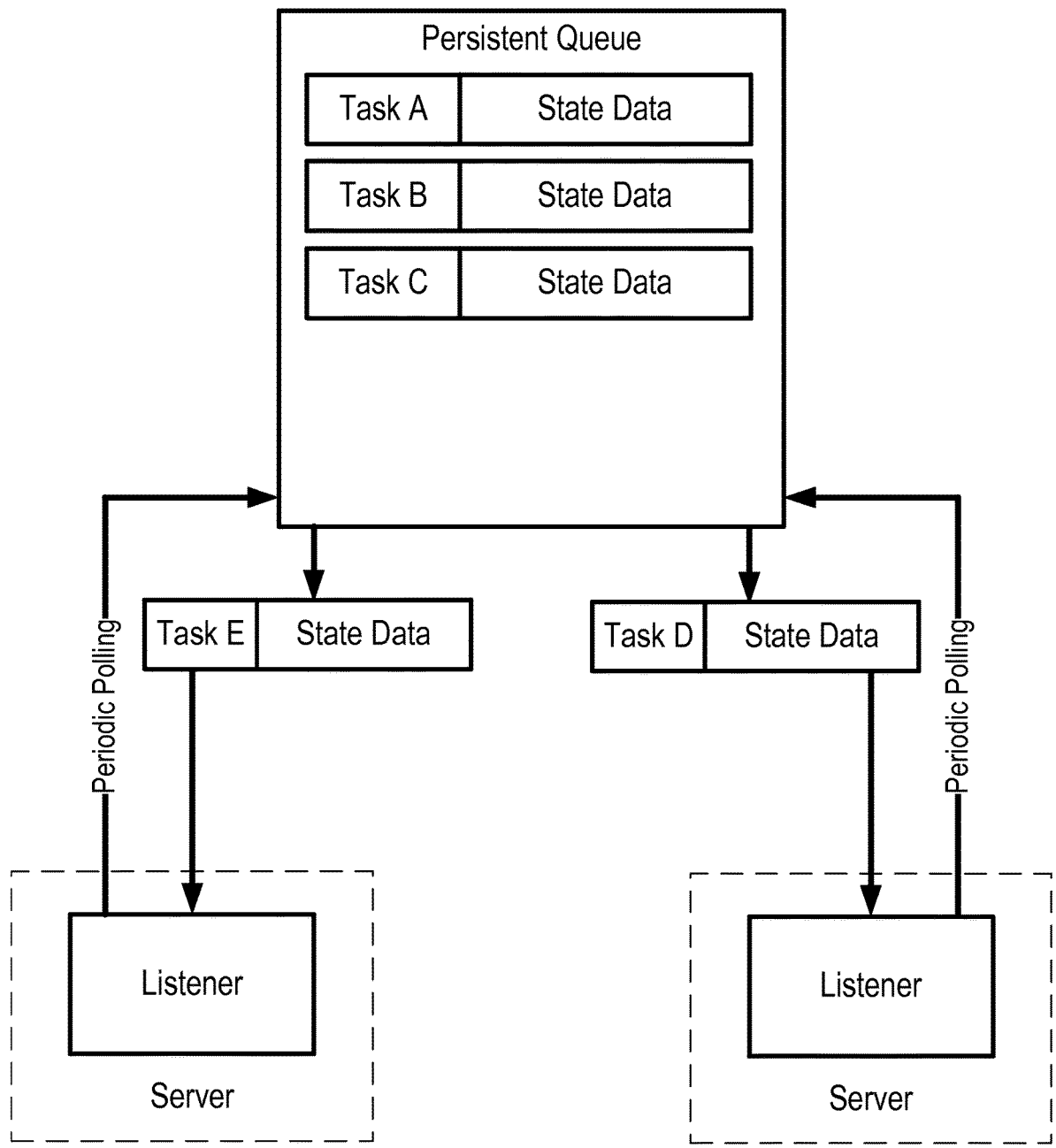
Figure 13:
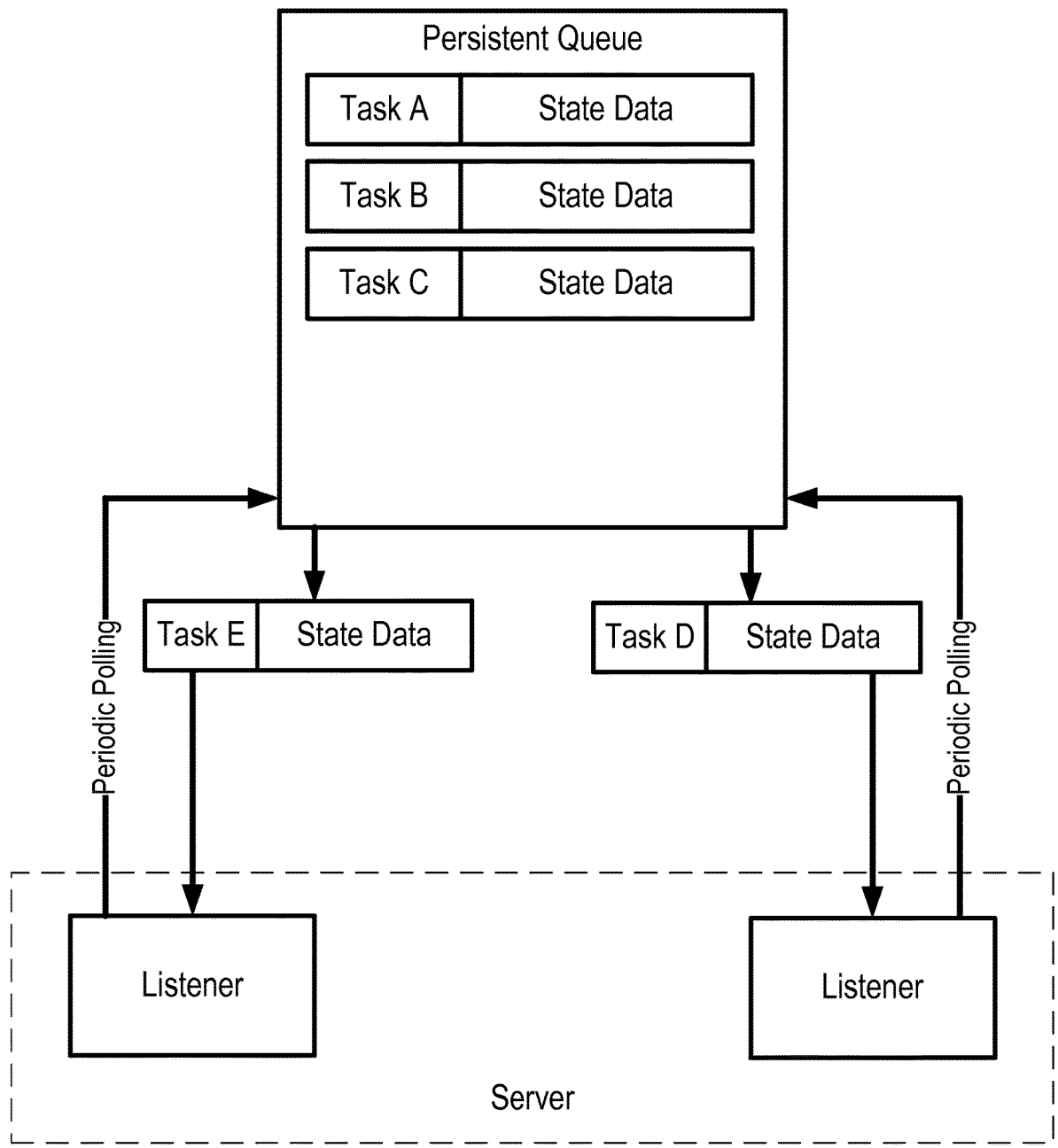

In one or more preferred implementations, tasks are stored in persistent queues and a current state is stored with the task, as illustrated in FIG. 8. The use of persistent queues and the storage of state data allows listeners to pick up discrete tasks and process them independently of other tasks, which in turn allows a system to be scaled out by adding additional listeners if needed. FIGS. 9-11 illustrate use of several listeners to process tasks of a persistent queue. These listeners may be running on separate servers, as illustrated in FIG. 12, or on the same server, as illustrated in FIG. 13.

Figure 14:
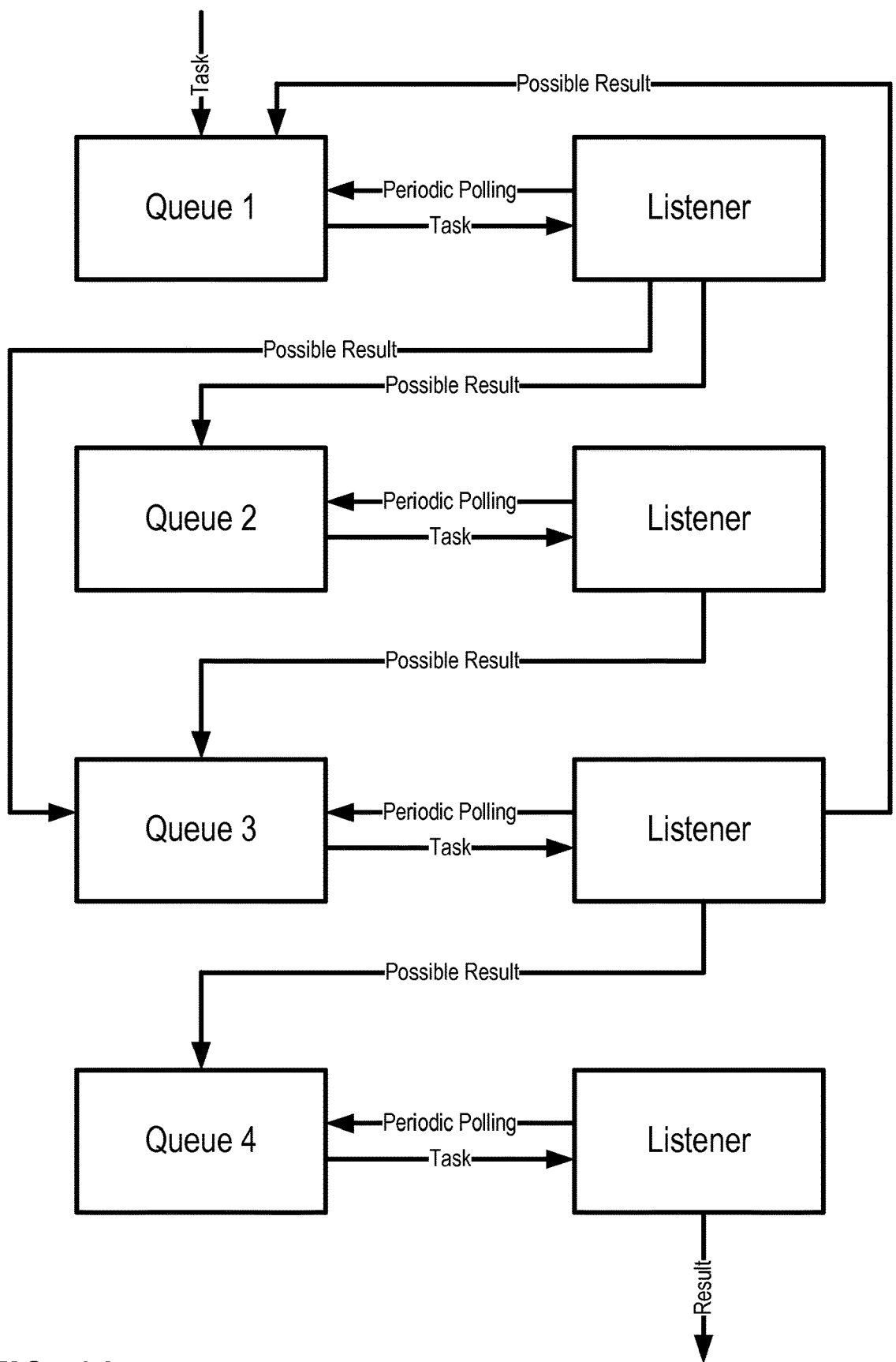
FIG. 14 illustrates use of four queues where processing of tasks received at each queue may result in various possible results.
Figure 15:
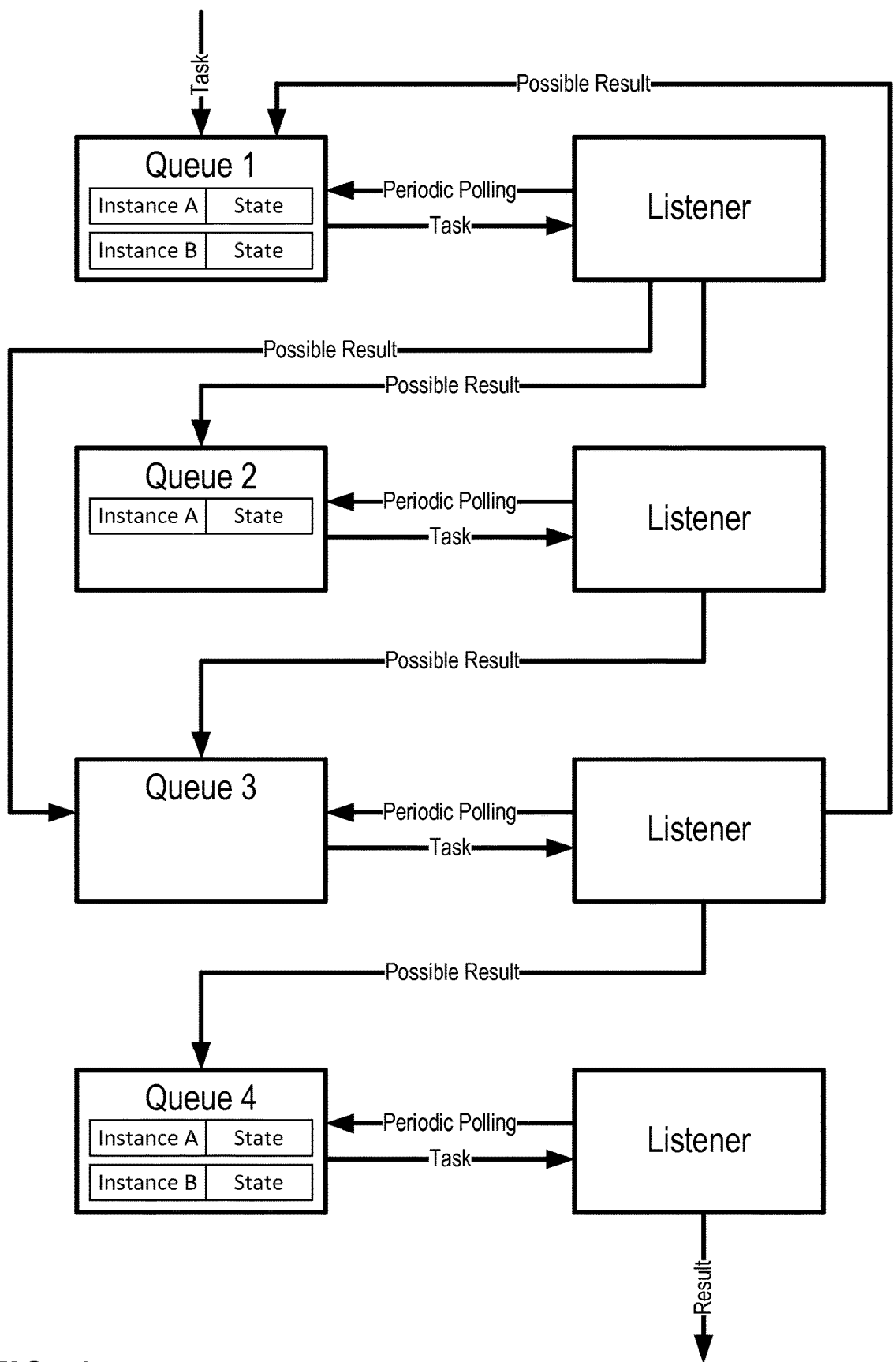
FIG. 15 illustrates the presence of various tasks at various queues at a point in time.

Although thus far described in the context of a linear process for illustrative purposes, it will be appreciated that methodologies described herein are applicable to more complicated processes as well. For example, FIG. 14 illustrates use of four queues for a slightly more complicated process where processing of tasks received at each queue may result in various possible results. At any given time, each of these queues may have various numbers of tasks ready to be sent to a listener, as illustrated in FIG. 15. In one or more preferred implementations, if one or more queues appear to be highly loaded, one or more additional listeners may be brought into the system.

It will be appreciated that methodologies described herein may be utilized in implementing much more complicated processes. For illustrative purposes, a methodology for use in a health care context will now be described.

Specifically, in one or more preferred implementations, methodologies described herein are utilized in a health care context to process health care workflows. In one or more preferred implementations, a methodology for processing health care workflows is implemented for a Windows Azure environment.

When a patient is receiving medical treatment, he or she may sometimes be presented with a care plan which will facilitate his or her treatment. The care plan may include instructions for one or more actions to perform or measurements to take outside of a health care professional's supervision. For example, a patient may be provided a care plan which includes instructions to weigh himself or herself every day, and record the results for eventual review by a health care professional.

Additionally, sometimes, a patient may be presented with a health care goal to meet. For example, a patient may be instructed to try to meet the goal of losing ten pounds over three months. This goal may include related instructions for the patient to weigh himself or herself every morning.

In one or more preferred implementations, methodologies disclosed herein are implemented for a monitoring and compliance application which improves patient engagement and collaboration between a patient and his or her health care provider. In an exemplary methodology, orders are created in an EHR for patients to perform home monitoring. The patient is notified of the order and the request will appear as a goal for the patient within a platform portal (such as, for example a web portal or a mobile application). The patient may comply with the order (which might be, for example, to monitor his or her weight daily) utilizing wireless devices (such as a Withings scale) that can communicate data to other devices or to the platform, or by manually entering values into the platform. This home monitoring data is then evaluated against patient specific rules that were configured when the order was placed. Non-compliance of the order or violation of any of the order parameters will result in a notification that is sent back to the ordering provider as a message in the EHR. The notification provides summary information about the order and results allowing the provider to determine if an intervention is necessary. Upon completion of the order, a summary of the results is sent back to the EHR for review by the provider.

Figure 16:
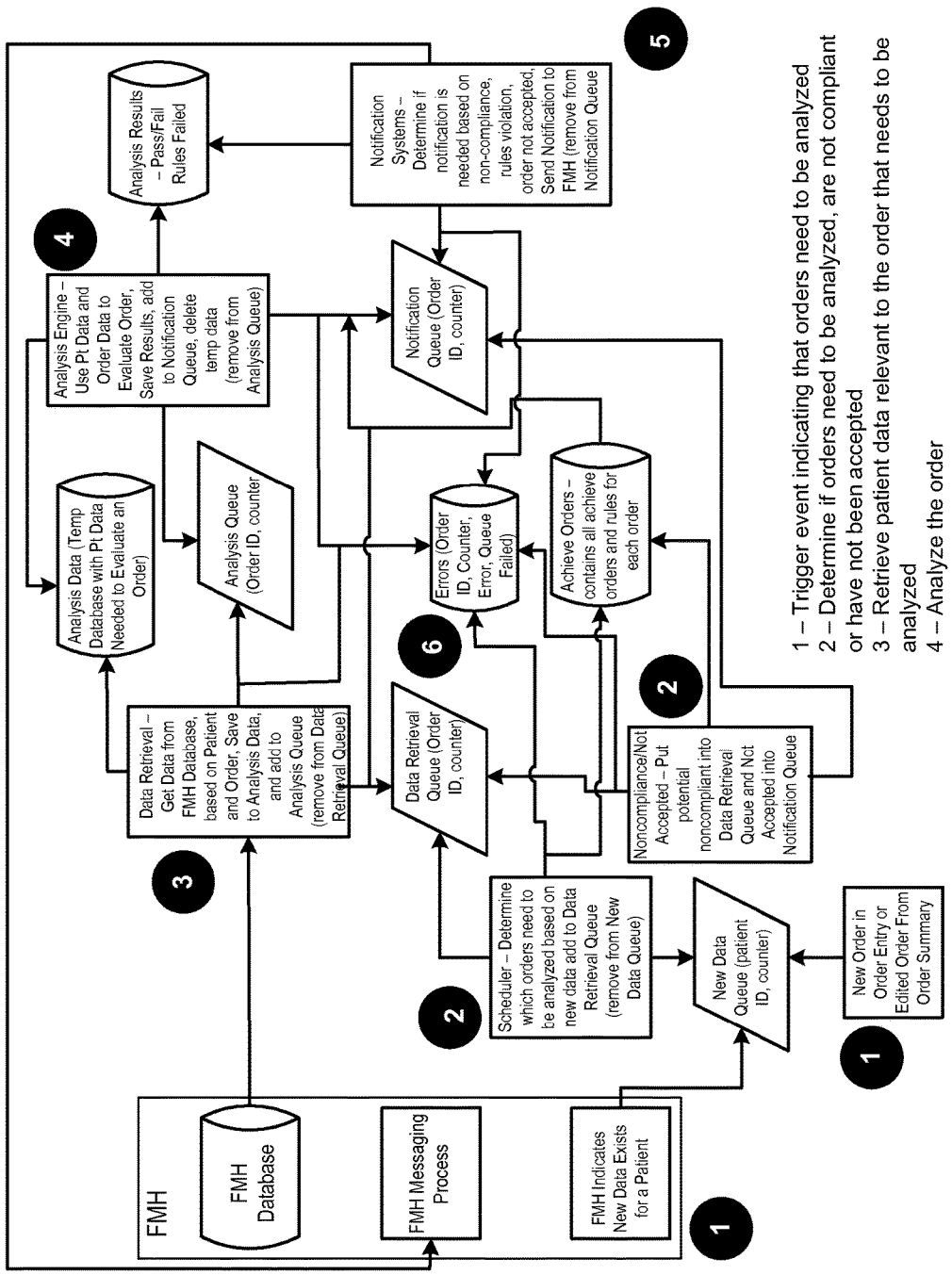
FIG. 16 illustrates an exemplary methodology for analyzing a health care order specified by a health care provider.

FIG. 16 illustrates an exemplary methodology for analyzing a health care order specified by a health care provider.

Systems and methodologies in accordance with one or more preferred implementations described herein support parallel processing of items (e.g. tasks). Further, systems and methodologies in accordance with one or more preferred implementations described herein support both scaling up and scaling out. For example, in accordance with one or more preferred implementations, resources can be added to existing servers, or new servers can be added. Additionally, each step of a workflow can be individually scaled.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A processor-based method comprising:
   (a) polling, via server polling, a first queue by a first queue listener associated with a first server;
   (b) receiving a first task and state information associated with the first task at the first queue listener in response to the polling by the first queue listener of the first queue;
   (c) executing, at the first server, the first task utilizing the state information associated with the first task;
   (d) electronically communicating a first result of the first task to a second queue, the first result including state information associated with the first task;
   (e) polling, via server polling, the second queue by a second queue listener associated with a second server;
   (f) receiving, at the second queue listener in response to the polling by the second queue listener of the second queue, a second task based on the first result communicated from the first server to the second queue, together with state information associated with the second task that is based on the state information included in the first result;
   (g) executing, at the second server, the second task utilizing the state information associated with the second task;
   (h) electronically communicating a second result of the second task to a third queue, the second result including state information associated with the second task;
   (i) polling, via server polling, the third queue by a third queue listener associated with a third server;
   (j) receiving, at the third queue listener in response to the polling by the third queue listener of the third queue, a third task based on the second result communicated from the second server to the third queue, together with state information associated with the third task that is based on the state information included in the second result;
   (k) executing, at the third server, the third task utilizing the state information associated with the third task; and
   (l) generating and electronically communicating a third result of the third task.

2. The processor-based method of claim 1, wherein the first server comprises an electronic device.

3. The processor-based method of claim 1, wherein the first server comprises one or more electronic devices.

4. The processor-based method of claim 1, wherein the second server comprises an electronic device.

5. The processor-based method of claim 1, wherein the second server comprises one or more electronic devices.

6. The processor-based method of claim 1, wherein the third server comprises an electronic device.

7. The processor-based method of claim 1, wherein the third server comprises one or more electronic devices.

8. The processor-based method of claim 1, wherein the method further comprises communicating a confirmation of completion of the first task.

9. The processor-based method of claim 1, wherein the method further comprises displaying, at a display associated with an electronic device, information to a user based on the third result.

10. The processor-based method of claim 1, wherein the method further comprises displaying, at a display associated with an electronic device, a notification to a user based on the third result.

11. The processor-based method of claim 1, wherein the method further comprises displaying, at a display associated with an electronic device, a notification associated with a patient health care order to a user based on the third result.

12. The processor-based method of claim 1, wherein the method further comprises displaying, at a display associated with an electronic device, a notification of a rule violation of a patient health care order to a user based on the third result.

13. The processor-based method of claim 1, wherein the method further comprises displaying, at a display associated with an electronic device, a notification associated with a patient health care order to a user.

14. The processor-based method of claim 1, wherein the method further comprises displaying, at a display associated with an electronic device, a notification of a rule violation of a patient health care order to a user.

15. The processor-based method of claim 1, wherein executing, at the third server, the third task utilizing the state information associated with the third task comprises determining whether a rule of a health care order has been violated.

16. The processor-based method of claim 1, wherein executing, at the third server, the third task utilizing the state information associated with the third task comprises effecting communication of a notification.

17. The processor-based method of claim 1, wherein executing, at the third server, the third task utilizing the state information associated with the third task comprises effecting communication of a notification that a rule of a health care order has been violated.

18. The processor-based method of claim 1, wherein executing, at the third server, the third task utilizing the state information associated with the third task comprises effecting communication of a notification that a patient is non-compliant with a health care order.

19. A processor-based method comprising:
(a) polling, via server polling, a first queue by a first queue listener associated with a first server;
(b) receiving a first task and state information associated with the first task at the first queue listener in response to the polling by the first queue listener of the first queue;
(c) executing, at the first server, the first task utilizing the state information associated with the first task;
(d) electronically communicating a first result of the first task to a second queue, the first result including state information associated with the first task;
(e) polling, via server polling, the second queue by a second queue listener associated with a second server;
(f) receiving, at the second queue listener in response to the polling by the second queue listener of the second queue, a second task based on the first result, together with state information associated with the second task that is based on the state information included in the first result;
(g) executing, at the second server, the second task utilizing the state information associated with the second task;
(h) electronically communicating a second result of the second task.

20. A non-transitory computer readable medium containing computer executable instructions for performing a method comprising:
(a) polling, via server polling, a first queue by a first queue listener associated with a first server;
(b) receiving a first task and state information associated with the first task at the first queue listener in response to the polling by the first queue listener of the first queue;
(c) executing, at the first server, the first task utilizing the state information associated with the first task;
(d) electronically communicating a first result of the first task to a second queue, the first result including state information associated with the first task;
(e) polling, via server polling, the second queue by a second queue listener associated with a second server;
(f) receiving, at the second queue listener in response to the polling by the second queue listener of the second queue, a second task based on the first result, together with state information associated with the second task that is based on the state information included in the first result;
(g) executing, at the second server, the second task utilizing the state information associated with the second task;
(h) electronically communicating a second result of the second task.

* * * * *